(12) United States Patent
Greyling et al.

(10) Patent No.: US 8,492,314 B2
(45) Date of Patent: Jul. 23, 2013

(54) AGRICULTURAL COMPOSITION WITH PH COLOUR INDICATORS

(75) Inventors: Hendrik Frederik Greyling, Bronkhorstspruit (ZA); Hugo R Minnaar, Kempton Park (ZA); Martin D Bloomberg, Toronto (CA)

(73) Assignee: AECI Limited, Sandton (ZA)

( * ) Notice: Subject to any disclaimer, the term of this patent is extended or adjusted under 35 U.S.C. 154(b) by 713 days.

(21) Appl. No.: 12/441,668

(22) PCT Filed: May 11, 2007

(86) PCT No.: PCT/IB2007/051791
§ 371 (c)(1),
(2), (4) Date: Oct. 28, 2009

(87) PCT Pub. No.: WO2008/035237
PCT Pub. Date: Mar. 27, 2008

(65) Prior Publication Data
US 2010/0120619 A1   May 13, 2010

(30) Foreign Application Priority Data
Sep. 18, 2006   (ZA) .............................. 2006/07788

(51) Int. Cl.
| | |
|---|---|
| *A01N 25/28* | (2006.01) |
| *A01N 31/02* | (2006.01) |
| *A01N 57/00* | (2006.01) |
| *A01N 47/28* | (2006.01) |
| *A01N 37/18* | (2006.01) |
| *A61K 31/66* | (2006.01) |
| *A61K 31/415* | (2006.01) |
| *A23K 1/18* | (2006.01) |
| *G01D 13/02* | (2006.01) |
| *G01D 21/00* | (2006.01) |

(52) U.S. Cl.
USPC ........... 504/359; 504/162; 504/165; 504/169; 504/171; 504/172; 504/173; 504/362; 116/206; 116/335; 424/10.3; 424/405; 424/438; 514/65; 514/68; 514/75; 514/109; 514/112; 514/115; 514/119; 514/120; 514/122; 514/134; 514/141; 514/142; 514/388

(58) Field of Classification Search
USPC ................ 504/359, 362, 162, 165, 169, 171, 504/172, 173; 116/206, 335; 424/10.3, 405, 424/438; 514/65, 68, 75, 109, 112, 115, 119, 514/120, 122, 134, 141, 142, 388
See application file for complete search history.

(56) References Cited

U.S. PATENT DOCUMENTS

| | | | |
|---|---|---|---|
| 5,278,132 A | 1/1994 | Fisher et al. | |
| 5,514,639 A | 5/1996 | Fisher et al. | |
| 6,500,447 B1 * | 12/2002 | Dexter et al. | 424/408 |
| 2006/0199739 A1 * | 9/2006 | Messerschmidt et al. | 504/357 |

FOREIGN PATENT DOCUMENTS

| | | |
|---|---|---|
| HU | 75012 A2 * | 3/1997 |
| WO | WO 99/25189 A1 | 5/1999 |

* cited by examiner

*Primary Examiner* — Jane C Oswecki
(74) *Attorney, Agent, or Firm* — Kilpatrick Townsend & Stockton LLP

(57) ABSTRACT

The present invention provides a concentrate for dilution with water in the preparation of an agricultural composition for application to crops, soil or animals. The concentrate is recommended for use with agricultural chemicals whose agricultural activity varies with the pH of the water. It comprises an active ingredient and a combination of pH indicators for coloring the water, the pH indicators being selected so as to indicate different colors of spray water at different pH levels. The proportions of active ingredient and pH indicators are selected so that when the concentrate is added to water, the pH indicators indicate visually upper and lower pH limits for optimum activity of the agricultural chemical.

18 Claims, No Drawings

AGRICULTURAL COMPOSITION WITH PH COLOUR INDICATORS

CROSS REFERENCE TO RELATED APPLICATIONS

This application is a National Stage of International Application No. PCT/IB2007/051791 filed May 11, 2007 and which claims the benefit of South African Patent Application No. 2006/07788 filed Sep. 18, 2006, the disclosures of all applications being incorporated herein by reference.

BACKGROUND OF THE INVENTION

This invention relates, broadly, to agricultural compositions. More particularly, it relates to a concentrate for dilution with water in the preparation of an agricultural composition, which concentrate is recommended for use with agricultural chemicals whose agricultural activity varies with the pH of the water.

Activity of the majority of agricultural chemicals varies with the pH of the water in which it is diluted in that they are sensitive to degradation under alkaline (high pH) or acidic (low pH) conditions. Very often the water that farmers use from boreholes, dams or rivers has a high pH and salt content (i.e. hard water), and is also influenced by seasonal changes and annual rainfall. This water tends to have a negative influence on the efficacy of pH sensitive agricultural chemicals in that the agricultural chemicals are hydrolysed to less active compounds. In these cases, the farmer or other user typically modifies pH of the water by adding to the water a suitable adjuvant, e.g. an acidic adjuvant when the water is too alkaline, or a basic adjuvant when the water is too acidic. In this way, optimal activity of the agricultural chemical is ensured.

In practice, water pH is measured and a suitable quantity of adjuvant is added to the water to obtain the desired pH. This involves making use of pH meters and pH indicator papers, which is a tedious operation. In addition, pH meters are very bulky, expensive, sensitive to transport and may be damaged during field use, whereas pH strips have a short shelf-life and become unreliable with varying temperatures, which are typical of field conditions.

The present invention seeks to avoid pH determinations or measurements, and to provide for automatic and immediate visual identification of a desired or an acceptable pH during preparation of the agricultural composition.

The applicant partially addressed this problem in its earlier patent ZA 87/0815. This patent covers a concentrate for use in the preparation of an aqueous agricultural composition and includes an active ingredient, typically a pH modifying agent, and a single pH indicator. The concentrate is added to the water carrier until the desired pH is reached, as shown by the pH indicator. However, if the user is not careful there is a danger of overdosing when using this concentrate. Once the water has changed colour at the desired pH, and more concentrate is accidentally or carelessly added, the pH of the water will continue to change although the colour of the water will remain the same. This may result in a spray mixture in which the pH of the water is no longer optimum for the particular agricultural chemical. Accordingly, this invention also seeks to avoid the danger of overdosing when adding a concentrate for dilution to water.

SUMMARY OF THE INVENTION

According to the invention there is provided a concentrate, to be diluted with water in the subsequent preparation of an agricultural composition that comprises an agricultural chemical with an activity which varies with the pH of the water, the concentrate comprising an active ingredient which may be an agricultural adjuvant for enhancing the activity of an agricultural chemical in an aqueous agricultural composition and/or an agricultural chemical with an activity which varies with the pH of water;

a first pH indicator arranged to undergo a colour change at a first pH; and a second pH indicator arranged to undergo a colour change at a second pH, different to the first pH, the first and second pH indicators providing an indication of respective lower and upper pH limits for acceptable agricultural activity of the agricultural chemical when the concentrate is diluted with water to provide an effective concentration of the active ingredient in the water.

The concentrate typically contains water, which acts as a diluent and carrier for the various ingredients in the concentrate.

The agricultural adjuvant is typically a pH modifying agent, selected from the group comprising acids, alkalis and buffers for controlling and modifying the pH of water.

In cases where the water is alkaline, the adjuvant may be any organic or inorganic acid and is preferably an acid selected from the group comprising acetic acid, orthophosphoric acid, nitric acid and the less preferred hydrochloric acid, sulphuric acid and formic acid.

If the water is too acidic, an alkaline modifying agent will be used. Examples of alkaline modifying agents include members of the group comprising ammonia, potassium hydroxide and sodium hydroxide.

In certain cases the adjuvant may be a buffer. The buffer may be a member of the group comprising ammonia, mono ammonium phosphate, mono potassium phosphate, phosphoric acid, sodium acetate and potassium hydrogen phthalate.

Instead of being an adjuvant, the active ingredient in the concentrate may be an agricultural chemical whose agricultural activity varies with the pH of water with which it is in contact.

In this case, i.e. when the concentrate contains the agricultural chemical whose activity varies with the pH of water with which it is in contact, the active ingredient may be selected from the group comprising pesticides, defoliants, desiccants and plant nutrients. Naturally, a pH colour indicator will be selected which is compatible or inert as regards the other constituents of the concentrate, in particular the agricultural chemical in the concentrate.

The active ingredient may be a pesticide, selected from the group comprising insecticides, nematocides, fungicides and herbicides; and possibly molluscicides and rodenticides. More particularly, the active ingredient may be selected from the group comprising organophosphates, carbamates, benzimidazoles, dicarboxamides, bipyridols, pyrethroids and chlorinated hydrocarbons. Newer and future agrochemical compounds are constantly being developed and these compounds are not excluded. Therefore any agrochemical compound with an activity which varies with the pH of water is included. Typical examples are azinphos methyl, benomyl, captan, dimethoate, ethyl parathion, methomyl, trichlorfon, oxamyl, dibrom, dimecron, mevinphos, monocrotophos, paraquat diquat, cypermethrin and dicofol. Of these, azinphos methyl, dimethoate, ethyl parathion, trichlorfon, dibrom, dimecron, mevinphos and monocrotophos are organophosphates; methomyl and oxamyl are carbamates; benomyl is a benzimidazole; captan is a dicarboxamide; paraquat and diquat are bipyridols; cypermethrin is a pyrethroid; and dicofol is a chlorinated hydrocarbon.

The pH indicators are preferably selected so that the intermediate colour, that is the overlapping colour of the lower end of the one pH indicator and the higher end of the other pH indicator, is the same.

The intermediate colour is preferably a so-called lighter colour, such as yellow, in order that the one pH indicator does not overshadow the other pH indicator.

The concentrate typically includes one or more wetting, spreading, adhesive or penetrating agents to provide improved leaf coverage, adhesion and penetration of a spray mixture including the concentrate, the correct quantity of wetting and other agents being indicated by the respective pH indicator.

DETAILED DESCRIPTION OF PREFERRED EMBODIMENTS

The present invention provides a concentrate for dilution with water in the preparation of an agricultural composition for application to crops, soil or animals. The concentrate is recommended for use with agricultural chemicals whose agricultural activity varies with the pH of the water. The concentrate for dilution with water in the preparation of an agricultural composition for application to crops, soil or animals, comprises an active ingredient and a combination of pH indicators for colouring the water. The pH indicators are selected so as to indicate different colours of the spray water at different pH levels. The proportions of active ingredient and pH indicators are selected so that when the concentrate is added to water, the pH indicators indicate visually upper and lower pH limits for optimum activity of the agricultural chemical. The present invention accordingly seeks not only to avoid pH determinations or measurements, and to provide automatic and immediate visual identification of the desired or an acceptable pH during preparation of the agricultural composition, but also to provide a guard against overdosing.

The concentrate typically contains water as a diluent to facilitate handling and measurement of the concentrate and to dissolve or disperse the various ingredients therein.

In one version of the invention, the active ingredient is an agricultural adjuvant for enhancing the activity of an agricultural chemical in an aqueous chemical composition. This adjuvant will typically be a pH modifying agent selected from the group comprising acids, alkalis and buffers for controlling and modifying the pH of water.

In areas where the available water is alkaline, the adjuvant may be an acid selected from the group comprising acetic acid, orthophosphoric acid, nitric acid and the less preferred hydrochloric acid, sulphuric acid and formic acid.

Naturally, if the available water is too acidic, an alkaline pH modifying agent will be employed. Examples of alkaline pH modifying agents include ammonia, potassium hydroxide and sodium hydroxide.

Instead of being an adjuvant, the active ingredient in the concentrate may be an agricultural chemical whose agricultural activity varies with the pH of water with which it is in contact.

In this case, in preparing the agricultural composition from the concentrate, the concentrate will be added to the water, and a separate adjuvant will typically be used, if necessary, in advance to modify the pH of the water to the desired value. Field staff will know in advance, from prior experimentation or usually from manufacturers' specifications and/or official regulations, what concentration of active ingredient is necessary for the agricultural composition in question i.e. appropriate dilution in water. The proportion of pH indicators in the concentrate will accordingly be related to the proportion of active ingredient therein so that, when an appropriate amount of concentrate is added to water in preparing the agricultural composition to provide the agricultural composition with the intended concentration of active ingredient, the composition will automatically contain sufficient proportions of the respective pH indicators for easy visual pH determination. The pH indicators in turn will be chosen so that they can indicate, by undergoing a colour change or by having a distinctive colour at a suitable pH, when the desired or acceptable pH has been attained. Field staff accordingly may simply add the appropriate or prescribed amount of the concentrate to the water, and, thereafter, add progressively increasing amounts of the appropriate adjuvant to the water until the appropriate colour change takes place, or the appropriate colour is attained.

In this case, i.e. when the concentrate contains the agricultural chemical whose activity varies with the pH of water with which it is in contact, the active ingredient may be selected from the group comprising pesticides, defoliants, desiccants and plant nutrients. Naturally, pH indicators will be selected which are compatible or inert as regards the other constituents of the concentrate, in particular the agricultural chemical in the concentrate.

The active ingredient may be a pesticide, selected from the group comprising insecticides, nematocides, fungicides and herbicides; and possibly iodophores (masked iodine), molluscicides and rodenticides. More particularly, the active ingredient may be selected from the group comprising organophosphates, carbamates, benzimidazoles, dicarboxamides, bipyridols, pyrethroids, and chlorinated hydrocarbons. Typical examples are azinphos methyl, benomyl, captan, dimethoate, ethyl parathion, methomyl, trichlorfon, oxamyl, dibrom, dimecron, mevinphos, monochrotophos, paraquat, cypermethrin and dicofol. Of these, azinphos methyl, dimethoate, ethyl parathion, trichlorfon, dimecron, mevinphos and monochrotophos are organophosphates; methomyl and oxamyl are carbamates, benomyl is a benzimidazole, captan is a dicarboxamide, paraquat is a bipyridol, cypermethrin is pyrethroid, and dicofol is a chlorinated hydrocarbon. These agrochemical compounds are merely examples and do not constitute an exhaustive list. Data published by the British Crop Protection Council (BCPC) can be referred to for pH sensitivity when mixed with water.

The active ingredient may also comprise (a) microelement(s) for foliar application. Examples of microelements, the uptake of which is optimum at pH levels of 4.5-5.5, include iron (Fe), manganese (Mn), boron (B), copper (Cu) and zinc (Zn).

The selection of the pH indicators is vital to the success of the formulation.

Combining two pH indicators to obtain two colour changes at two different pH levels may seem a simple task, but it is not. A pH indicator normally works in a limited pH range of up to two units. Above a certain pH, it will be a certain colour and, upon pH modification, the colour will change over 1 to 2 pH units. Above or below these pH units it will remain that particular colour. To illustrate this point, one can use the example of the pH indicator litmus. Above a pH of 8.0, the colour is blue and below a pH of 5.0, it is red. Outside of these pH parameters of 8.0 and 5.0, it will remain blue and red, respectively. When combining litmus with another pH indicator that has its activity below a pH of 5.2 (e.g. methyl orange—yellow at pH 4.6 and red at pH 3.2), litmus will tend to dominate the other pH indicator and it will be virtually impossible to see the effect of the second pH indicator as the colour of the water solution will stay largely red.

To address this problem the invention provides for the selection of pH indicators which are compatible with one another. The indicators are thus chosen in such a way that the lower end of the one pH indicator's colour is the same as the higher end of the other pH indicator's colour, referred to as the intermediate colour. Furthermore, this intermediate colour should be of a light colour such as yellow. If the intermediate colour is of a darker nature, such as blue or red, the one pH indicator again will dominate the other with the result that the second colour change of the water will not be visible.

Of further importance to the success of a double colour change at two different pH levels, is the ratio in which different quantities of the two indicators is mixed. Different pH indicators have different colour intensities and should therefore be mixed in the correct ratio as to make sure that the colour transitions are visible to an untrained eye of a farmer or any other user. The correct ratio of indicators becomes furthermore important as this concentrate is added to both soft and hard waters. In hard and/or alkaline waters, more of the concentrate is needed to obtain an optimum pH level than in soft waters.

For agricultural chemicals sensitive to alkaline hydrolysis, the pH indicators may be selected from the following groups and combined in different ratios as set out below:

i) For a colour transition of green to yellow to orange/red:
Select one or more indicator(s) from each of the following groups.
Group 1: Bromoxylenol blue (blue at pH 7.4 and yellow at pH 5.6)
Bromocresol green (blue at pH 5.6 and yellow at pH 4.0)
Group 2: Methyl yellow (yellow at pH 4.5 and red at pH 3.2)
Methyl orange (yellow at pH 4.5 and red at pH 3.2)
Naphtyl red (yellow at pH 5.0 and red at pH 3.7)

The indicators from group 1 can be used at 0.05-0.20 parts by mass of the concentrate, whilst the indicators from group 2 can be selected at 0.10-0.50 parts per mass of the concentrate. In general, the pH indicator at the higher end of the pH scale (in this case group 1) is used at a lower ratio to the pH indicator at the lower end of the scale (in this case group 2).

ii) For a colour transition of purple to yellow to orange/red:
Select one or more indicator(s) from each of the following groups.
Group 3: Bromophenol red (purple at pH 7.0 and yellow at pH 5.2)
Chlorophenol red (purple-red at pH 6.6 and yellow at pH 5.2)
Alizarin red (red at pH 6.4 and yellow at pH 4.4)
Cochineal (purple at pH 6.2 and yellow at pH 4.8)
Group 4: Methyl yellow (yellow at pH 4.5 and red at pH 3.2)
Methyl orange (yellow at pH 4.5 and red at pH 3.2)
Naphtyl red (yellow at pH 5.0 and red at pH 3.7)

The indicators from group 3 can be used at 0.05-0.30 parts by mass of the concentrate, whilst the indicators from group 4 can be selected at 0.10-0.50 parts per mass of the concentrate. In general, the pH indicator at the higher end of the pH scale (in this case group 3), is used at a lower ratio to the pH indicator at the lower end of the scale (in this case group 4).

For agricultural chemicals sensitive to acid hydrolysis (i.e. below a pH of 6) such as some copper fungicides, the pH indicators may be selected from the following groups and combined in different ratios as set out below:
Group 5: Xylenol blue (blue at pH 9.5 and yellow at pH 8.0)
o-Cresol red, alkaline range (red at pH 8.8 and yellow at 7.2)
m-Cresol purple, alkaline range (purple at pH 9.2 and yellow at pH 7.6)
1-Naphtolbenzein (green at pH 9.8 and yellow at pH 8.4)
Group 6: Neutral Red (yellow pH 8.0 and red at pH 6.8)

The indicators from groups 5 and 6 can be used at 0.10-0.50 parts by mass of the concentrate. Thus, in this case the indicators from each group can be mixed in similar amounts.

The indicators as listed in groups 1 to 6 are not an exhaustive group but these indicators were found in practice to give the best results. Literature will show that there are other indicators that will fall into the same criteria as listed in groups 1 to 6, but these did not provide optimum results when tested in the concentrate.

The concentrate for dilution may, in addition to the active ingredient and pH indicators, also contain one or more wetting agents. The function of a wetting agent is to lower the surface tension of the spray water. Due to the waxy nature of leaf surfaces, it has a natural repulsion effect on water and will result in a less effective uptake of pesticides and/or nutrients contained in the spray mixture. By adding a wetting agent, better coverage of the spray mixture on the leaf surface is ensured resulting in better uptake of nutrients and pesticides.

As mentioned previously, it is a well known that the activity of certain agricultural chemicals varies not only with the pH of the water, but also the hardness thereof. Hard water is typically the result of the interaction of metals, such as calcium and magnesium, with carbonates and bicarbonates. Less well known is that metals found in hard water also react with wetting agents that are widely used in the agrochemical industry. The effect that metals have on wetting agents can be illustrated by the example of a dirty ring around a bath tub. The dirty ring is the result of calcium and magnesium ions reacting with soap anions to produce insoluble soap curds. A similar effect occurs when wetting agents, which are largely made-up of soap anions, are used in hard waters. This underlines the fact that more wetting agents are required in areas with hard waters than in areas with softer waters due to the presence of metal anions that render part of the wetting agent inactive. Optimum wetting is of crucial importance to ensure spreading and penetration of spray mixtures containing pesticides and nutrients.

The pH indicators in the concentrate for dilution thus play an additional role. They also indicate when appropriate levels of wetting agent is present in the spray mixture. The concentrate for dilution is formulated in such a way that the ratio of pH modifying agents and wetting agents is such that when added to both soft and hard waters, the optimum level of active ingredients and wetting agents are achieved.

The addition of wetting agents to spray mixtures is normally recommended at fixed rates. This will mean that in some instances (e.g. in areas with hard waters) insufficient quantities of wetting agents are present in the spray mixtures, resulting in insufficient spreading and uptake of pesticides and/or nutrients. In softer waters, however, there will invariably be an excess of wetting agents present, resulting in a financial loss for the farmer.

The inclusion of a second pH indicator for reducing the risk of overdosing of the active ingredient thus extends to the wetting agents as well.

The invention will now be illustrated by the following non-limiting example.

Example

| Constituent | Parts Per Mass |
| --- | --- |
| Wetting agent - Nonyl phenol polyoxyethyleneglycol (9 moles of ethylene oxide) | 25 parts per mass |
| Acid adjuvant - Orthophosphoric acid | 35 parts per mass |
| Wetting agent and solvent - Glycol | 20 parts per mass |
| Diluent and carrier - Water | 19.7 parts per mass |
| Indicators - Bromocresol green and Methyl yellow | 0.1 parts per mass and 0.2 parts per mass, respectively |

It was found that the above concentrate, when added to water, provides mixtures whose pH can easily be visually determined by the colour change from blue to yellow at a pH of about 5.0-5.5, as indicated by the bromocresol green, and the colour change from yellow to orange/red at a pH of about 3.0-3.5, as indicated by the methyl yellow. This thus provides a clear indication of when the pH of the water is suitable for agricultural activity of the pH sensitive agricultural chemical microelement uptake whilst also providing an indication of when overdosing of the concentrate has taken place.

An additional advantage of pH colour changes taking place at different pH levels, is that a farmer is provided with a wider spectrum of pH colour changes of the water when preparing a spray solution containing an agricultural chemical. Thus, although certain chemicals have an agricultural activity at a slightly acidic pH of 4 to 6, there are exceptions. Some agricultural chemicals have optimum agricultural activity at a pH as low as 3 to 3.5 (example the herbicide glyphosate). Likewise, certain bound copper fungicides such as cupric hydroxide have an optimum agricultural activity at a pH of about 8. By combining two pH indicators, it is also possible to visually indicate the pH at two pH levels and, hence, the suitability for a wider range of agricultural chemicals.

Apart from being sensitive to alkaline hydrolysis, certain herbicides are also very sensitive to the presence of salts in hard water. Herbicide antagonism from salts depends on the ions present and the concentration of these ions in water. These salts react with the herbicide to chemically modify it. The following herbicides are examples of herbicides being influenced by salts in hard waters: glyphosaste, glyphosate trimesium, 2,4-Dichlorophenoxy acetic acid, dicamba-dimethyl amine, tralkoxydim and sethoxydim.

Phosphoric acid (and sulphuric acid to a lesser extent) is known to neutralise the effect that salts in hard waters have on herbicides. By including the appropriate amounts of phosphoric acid together with the correct combination of pH indicators, the farmer or any other user is assured when adding the concentrate to a spray mixture to the first colour change, there is enough phosphoric acid present to neutralise harmful salts.

Although the above invention has been described with particular reference to two pH indicators, it is envisaged that more than two indicators could be used, although the issue of compatibility becomes more difficult the greater the number of indicators.

The invention claimed is:

1. A concentrate, to be diluted with water in the preparation of an agricultural composition that comprises an agricultural chemical with an activity which varies with the pH of the water, the concentrate comprising— an active ingredient which is an agricultural adjuvant for enhancing the activity of an agricultural chemical in an aqueous agricultural composition and/or an agricultural chemical with an activity which varies with the pH of water;

a first pH indicator arranged to undergo a colour change at a first pH; and a second pH indicator arranged to undergo a colour change at a second pH, different to the first pH, the first and second pH indicators providing an indication of an appropriate pH between the first pH and the second pH at which the agricultural chemical is active when the concentrate is diluted with water to provide an effective concentration of the active ingredient in the water.

2. A concentrate according to claim 1 wherein the pH indicators are selected so that an intermediate colour, that is an overlapping colour of the first pH indicator and of the second pH indicator, is the same.

3. A concentrate according to claim 2 wherein the intermediate colour is selected such that the one pH indicator does not overshadow the other pH indicator.

4. A concentrate according to claim 1 wherein the concentrate contains water, which acts as a diluent and carrier for the ingredients in the concentrate.

5. A concentrate according to claim 1 wherein the active ingredient is an agricultural adjuvant for enhancing the activity of an agricultural chemical in an aqueous agricultural composition and wherein the agricultural adjuvant is a pH modifying agent.

6. A concentrate according to claim 5 wherein the agricultural adjuvant is selected from the group consisting of acids, alkalis and buffers for controlling and modifying the pH of water.

7. A concentrate according to claim 6 wherein the agricultural adjuvant is an organic or inorganic acid selected from the group consisting of acetic acid, orthophosphoric acid, nitric acid, hydrochloric acid, sulphuric acid and formic acid.

8. A concentrate according to claim 6 wherein the agricultural adjuvant is an alkaline modifying agent selected from a the group consisting of ammonia, potassium hydroxide and sodium hydroxide.

9. A concentrate according to claim 6 wherein the agricultural adjuvant is a buffer selected from the group consisting of ammonia, mono ammonium phosphate, mono potassium phosphate, phosphoric acid, sodium acetate and potassium hydrogen phthalate.

10. A concentrate according to claim 1 wherein the active ingredient is an agricultural chemical with an activity which varies with the pH of water with which it is in contact and wherein the active ingredient is selected from the group consisting of pesticides, defoliants, desiccants and plant nutrients.

11. A concentrate according to claim 1 wherein the pH indicator is compatible with or inert with respect to other constituents of the concentrate.

12. A concentrate according to claim 10 wherein the active ingredient is a pesticide selected from the group consisting of insecticides, nematocides, fungicides, herbicides, molluscicides and rodenticides.

13. A concentrate according to claim 12 wherein the active ingredient is selected from the group consisting of organophosphates, carbamates, benzimidazoles, dicarboxamides, bipyridols, pyrethroids and chlorinated hydrocarbons.

14. A concentrate according to claim 13 wherein the active ingredient is selected from a group consisting of azinphos methyl, dimethoate, ethyl parathion, trichlorfon, dibrom, dimecron, mevinphos and monocrotophos; methomyl and oxamyl benomyl; captan; paraquat and diquat; cypermethrin; and dicofol.

15. A concentrate according to claim 1 wherein the concentrate also includes one or more wetting, spreading, adhesive and/or penetrating agents to provide improved leaf coverage, adhesion and penetration of a spray mixture, including the concentrate.

16. An agricultural composition including a concentrate according to claim 1 for application to crops, soil or animals.

17. A method of preparing an aqueous agricultural composition for application to crops, soil or animals, and which comprises an agricultural chemical with an activity which varies with the pH of the water with which it is in contact, the method comprising admixing with the water a concentrate according to claim 1 and the agricultural chemical, the concentrate comprising an adjuvant which is a pH modifying agent that modifies the pH of the composition.

18. A method of preparing an aqueous agricultural composition for application to crops, soil or animals, and which comprises an agricultural chemical with an activity which varies with the pH of the water with which it is in contact, the method comprising admixing with the water a concentrate according to claim 1, the concentrate comprising an agricultural chemical so that adding the concentrate to the composition acts to provide an agriculturally effective concentration of the agricultural chemical in the composition, and a pH modifying agent to obtain a pH in the composition of the agricultural chemical which is active.

* * * * *